United States Patent [19]

Mason

[11] Patent Number: 5,637,468
[45] Date of Patent: Jun. 10, 1997

[54] SALT STABILIZATION OF ANTIBODY-ENZYME CONJUGATES HEAT-DRIED INTO PAPER

[75] Inventor: Karen L. Mason, Edina, Minn.

[73] Assignee: Immunomatrix, Inc., Gaithersburg, Md.

[21] Appl. No.: 531,477

[22] Filed: Sep. 21, 1995

Related U.S. Application Data

[62] Division of Ser. No. 97,859, Jul. 26, 1993, Pat. No. 5,468,622, which is a continuation of Ser. No. 504,116, Apr. 3, 1990, abandoned.

[51] Int. Cl.⁶ .................. G01N 33/531; G01N 33/535; G01N 33/543; G01N 33/558
[52] U.S. Cl. .................. 435/7.9; 422/56; 422/57; 427/2.11; 427/2.13; 427/372.2; 427/394; 427/395; 435/4; 435/7.92; 435/7.93; 435/188; 435/287.1; 435/287.2; 435/287.9; 435/805; 436/514; 436/518; 436/527; 436/528; 436/529; 436/530; 436/531; 436/810
[58] Field of Search ............... 422/56–58; 427/2.11, 427/2.13, 372.2, 394–396; 435/4, 7.9, 7.92, 7.93, 188, 287.1, 287.2, 287.7, 287.9, 805, 810, 970; 436/514, 518, 527, 528, 529, 530, 531, 169, 810

[56] References Cited

U.S. PATENT DOCUMENTS

| | | | |
|---|---|---|---|
| 2,897,600 | 8/1959 | Graham et al. | 435/136 |
| 3,451,935 | 6/1969 | Roald et al. | 252/135 |
| 3,607,653 | 9/1971 | Ziffer | 195/63 R |
| 3,629,123 | 12/1971 | O'Reilly et al. | 252/89 |
| 3,723,327 | 3/1973 | Van Kampen et al. | 252/110 |
| 3,746,621 | 7/1973 | Kondo et al. | 195/63 |
| 3,764,477 | 10/1973 | Lehmann et al. | 195/63 |
| 3,773,674 | 11/1973 | Adams et al. | 252/99 |
| 3,796,634 | 3/1974 | Haynes et al. | 195/63 |
| 3,860,484 | 1/1975 | O'Malley | 195/63 |
| 3,876,504 | 4/1975 | Koffler | 195/103.5 R |
| 3,983,000 | 9/1976 | Messing et al. | 195/63 |
| 4,002,532 | 1/1977 | Weitman et al. | 195/103 |
| 4,009,076 | 2/1977 | Green et al. | 196/63 |
| 4,011,169 | 3/1977 | Diehl et al. | 252/95 |
| 4,024,000 | 5/1977 | Shibata et al. | 195/63 |
| 4,066,512 | 1/1978 | Lai et al. | 195/127 |
| 4,081,329 | 3/1978 | Jaworek et al. | 195/63 |
| 4,169,012 | 9/1979 | Dawson et al. | 435/188 |
| 4,228,240 | 10/1980 | Dawson et al. | 435/188 |
| 4,233,405 | 11/1980 | Neubeck | 435/187 |
| 4,235,973 | 11/1980 | Tschang et al. | 521/146 |
| 4,280,816 | 7/1981 | Elahi | 23/230 B |
| 4,318,990 | 3/1982 | Thomson et al. | 435/219 |
| 4,331,761 | 5/1982 | Dawson et al. | 435/188 |
| 4,391,904 | 7/1983 | Litman et al. | 435/7 |
| 4,409,105 | 10/1983 | Hayashi et al. | 210/679 |
| 4,446,232 | 5/1984 | Liotta | 435/7 |
| 4,517,288 | 5/1985 | Giegel et al. | 435/7 |
| 4,563,425 | 1/1986 | Yoshioka et al. | 435/94 |
| 4,623,618 | 11/1986 | Rokugawa | 435/6 |
| 4,757,016 | 7/1988 | Klenner et al. | 435/188 |
| 4,764,466 | 8/1988 | Suyama et al. | 435/174 |
| 4,806,343 | 2/1989 | Carpenter et al. | 424/450 |
| 4,806,478 | 2/1989 | Stahl | 435/180 |
| 4,824,938 | 4/1989 | Koyama et al. | 530/351 |
| 4,837,395 | 6/1989 | Leeder et al. | 436/810 |

FOREIGN PATENT DOCUMENTS

| | | | |
|---|---|---|---|
| 0340693 | 6/1972 | U.S.S.R. | 435/188 |

*Primary Examiner*—Christopher L. Chin
*Attorney, Agent, or Firm*—Fay, Sharpe, Beall, Fagan, Minnich & McKee

[57] ABSTRACT

New and useful methods of producing stabilized enzyme antibody conjugates are disclosed which are particularly useful in forming multi-layer immunoassay test devices. In particular, the invention concerns the formation of a manganese ion and enzyme-antibody conjugate in aqueous solution and drying the solution to produce a dry stabilized enzyme-antibody conjugate. Further, this stabilized enzyme-antibody conjugate can be formed on a continuous web and dried in a heat tunnel. This continuous manufacturing process allows for the more efficient production of multi-layer test strips.

33 Claims, No Drawings

SALT STABILIZATION OF ANTIBODY-ENZYME CONJUGATES HEAT-DRIED INTO PAPER

This is a divisional of application Ser. No. 08/097,859 filed on Jul. 26, 1993, now U.S. Pat. No. 5,468,622; which is a continuation of application Ser. No. 07/504,116 filed on Apr. 3, 1990, now abandoned.

BACKGROUND OF THE INVENTION

This invention relates to a method of producing stable immunoassay reagents. More particularly, it relates to a test strip upon which is deposited stabilized enzyme antibody conjugates. Enzyme-based diagnostic assays are used to test for the presence of antigens or antibodies in human body fluids. Many methods are used including the use of liquid reagents, radioimmunoassay methods, the use of dry test strips, and the use of coated test slides. U.S. Pat. No. 3,876,504 to Koffler teaches the use of a glass or plastic slide coated with a gelatin and a porous surface forming material to which is bonded either component of the antibody-antigen reaction of interest in an insolubilized form. The slide is air dried and desiccated. The other component, either antigen or antibody, is conjugated with an enzyme, and this conjugate is mixed with the body fluid to be applied to the slide. A coloring agent activatible by the enzyme is finally applied to the test slide in order to provide an indication of antibody-antigen reaction.

The reagents and indicators for immunoassay are fragile and often deteriorate in normal storage operation conditions. Several methods have been attempted to achieve a more stabilized reagent. U.S. Pat. No. 3,860,484 to O'Malley discloses a process of stabilization of unconjugated enzymes by contacting them with synthetic polymers and copolymers. The resulting solution is then freeze dried to form a dry product.

U.S. Pat. No. 4,806,343 to Carpenter et al discloses a method for preserving the activity of proteins after freezing by exposing the protein to a carbohydrate and a transition metal ion and then freezing the protein. Useful metal ions discussed include divalent ions of Zn, Cu, Cd, Ni, and Co.

U.S. Pat. No. 4,563,425 to Yoshioka et al discloses a method to inhibit enzyme deactivation when the enzyme is contacted with a glucose based substrate solution. This method involves the addition of carrier bound metalions to the substrate solution before termination of the enzyme substrate reaction. The metal ion may be one or more of Ti, V, Cr, Mn, Fe, Co, Cu, Sb, Ce, or Ag. The metal salt may be an acid salt or a complex salt, such as a halogen salt. The carrier may be, for example, a polysaccharide, polyamide, glass, or ion exchanger.

U.S. Pat. No. 4,024,000 to Shibata et al discloses a method for the stabilization of an aqueous solution of unconjugated beta-amylase enzyme during purification by adding a divalent or trivalent metal ion to the solution. The resulting solution is then purified by membrane separation at 45°–55° C. After separation, the concentrated enzyme solution may be salted out by addition of sodium chloride, in order to precipitate a beta-amylase fraction, which may then be dried.

U.S. Pat. Nos. 4,331,761; 4,169,012; and 4,228,240 to Dawson et al disclose a method for stabilizing aqueous peroxidase containing compositions by the addition of polyvalent metal ions to the compositions. Such ions may include Mg, Ca, Sc, Ti, V, Cr, Mn, Fe, Co, Ni, Cu, Zn, Ga, and Al. The metal salts may be sulfates, phosphates, halides, or nitrates. The products of the various Dawson et al patents may be either dried or in aqueous solutions. The dried products are disclosed to be dried from aqueous compositions which then may or may not be lyophilized. However, the compositions are usually first lyophilized.

U.S. Pat. No. 4,757,016 to Klenner et al discloses a process for stabilization of a peroxidase enzyme which may be conjugated to an antibody. This is done by incubation of the enzyme with aminopyrine for one hour at 20°–25° C.

U.S. Pat. No. 4,233,405 to Neubeck discloses a spray drying process for preparation of unconjugated enzyme products. Neubeck discloses the concentration of a liquid enzyme solution by ultrafiltration and the addition of water-insoluble salts to the concentrate prior to the spray drying.

Finally, U.S. Pat. No. 4,446,232 to Liotta discloses dry, layered test strips suitable for use in enzyme-linked immunoabsorbant assays (ELISA), having a layer of porous material such as nitrocellulose or DBM paper within which soluble enzyme-linked antibodies are dispersed. However, the only method disclosed by Liotta for application of the enzyme-linked antibodies to the test strip is lyophilization.

Therefore, what is needed is a high temperature stable enzyme-antibody conjugate. What is also needed is a continuous method to produce storage stable dry, test strip layers suitable for use in ELISA.

SUMMARY OF THE INVENTION

The present invention relates to a method for stabilizing the activity of a dry enzyme-antibody conjugate comprising forming an aqueous solution of an enzyme-antibody conjugate and a source of manganese ion and drying the solution at an elevated temperature and ambient pressure to form a manganese ion stabilized conjugate. In another embodiment, the present invention relates to a continuous method for the manufacture of a stabilized, dry test strip for immunoassay comprising forming an aqueous solution of an enzyme-antibody conjugate and a source of a manganese ion, contacting a continuous web with the solution and drying the web at elevated temperatures and ambient pressure. The term "stability of enzyme activity" as used herein the specification and the claims means increasing the activity of the stored enzyme significantly above that of an untreated enzyme. The term "antibody stability" as used herein the specification and the claims means increasing the antibody binding activity significantly above that of an untreated antibody. The term "conjugate" as used herein the specification and the claims means a physical coupling, e.g., covalent binding, of the antibody and enzyme. The phrase "drying at elevated temperatures" as used herein the specification and the claims means drying of a substance at temperatures greater than room temperature.

DETAILED DESCRIPTION OF THE PREFERRED EMBODIMENT

I have found that it is possible to stabilize an enzyme-antibody conjugate by adding manganese ions in an aqueous solution and thermally drying the solution. This is preferably accomplished through the addition of a manganese ion source to an aqueous enzyme-antibody solution. Preferably, enough metal ion source is added to form an aqueous solution of up to about 1M of manganese ion. More preferably, the manganese source is added to solution at about 50 mM to about 500 mM. However, the order of addition is not critical. The enzyme-antibody may also be added to a manganese ion source containing solution. The metal ion source is preferably introduced as a salt; sulfates and halogens are more preferred, and chlorides are most preferred.

This invention may be used to stabilize enzyme-antibody conjugates generally. More preferably, the enzyme-antibody conjugate stabilized is an antibody conjugated with horseradish peroxidase (HRP), and most preferably, HRP is conjugated with an antibody specific for theophylline. The enzyme-antibody conjugate may be prepared by any means known by those skilled in the art. One method is the standard periodate method of Wilson and Nakame mentioned in the Liotta patent.

Once the manganese ion source and conjugate have been mixed in the aqueous solution, the solution is introduced to elevated temperatures for drying. Preferably, the drying is done at temperatures from about 40° C. to about 100° C. More preferably, the drying is performed between about 55° C. and about 80° C. Convection, conventional, infrared, heat tunnel, and microwave ovens are preferred as sources of elevated temperatures. More preferably, a heat tunnel is used. Most preferably, a heat tunnel with a plurality of heating zones is used.

The manganese ion stabilized enzyme-antibody conjugate may be dried for use in any manner. It is preferred that the conjugate is dried onto a substrate. More preferably, the substrate is paper, glass, fiberglass, agarose, nitrocellulose, polymeric materials, or mixtures thereof. Most preferably, the substrate is paper, nylon, dacron, fiberglass, agarose, nitrocellulose, polyacrylamide, or mixtures thereof. This substrate is preferred in a woven, non-woven, or a sheet form. Most preferably, the stabilized conjugate is dried onto a substrate and incorporated into a Liotta-type test strip as disclosed in U.S. Pat. No. 4,446,232 described above and incorporated herein by reference.

The invention is preferably practiced by forming the enzyme-antibody conjugate/manganese ion aqueous solution and introducing into the solution a continuous web of a substrate, allowing the solution to saturate the substrate. The saturated substrate is then removed from the solution and drawn through a heat tunnel to dry. The heat tunnel preferably has a plurality of zones of differing heat levels. The first zone is preferably the hottest and the last zone is preferably the coolest. Upon removal from the heat tunnel, the continuous web is preferably cut into several smaller pieces of test material. These test pieces are most preferably incorporated into a Liotta-type strip.

EXAMPLES

The present invention is demonstrated by the following examples. These are merely illustrative; obvious modifications can be carried out in light of the previous discussion and appended claims. All percentages and proportions referred to in this description are by weight unless otherwise indicated.

In the Examples, the following material and methods were used.

A. The enzyme-antibody conjugate:

A fragment of a monoclonial antibody specific for theophylline was conjugated to horseradish peroxidase (HRP). This was purified and kept at −80° C. as a conjugate concentrate until used.

B. Base formulation for impregnation into paper:
HEPES buffer, 100 mM, pH 7.
Ovalbumin, 1%
Mannitol, 2.5%
Rabbit antitheophylline antiserum (See application Ser. No. 07/284,099)

C. Drying parameters:
Dryer: 3 zones, 18 feet long
Temperature:
zone 1=175° F.
zone 2=160° F.
zone 3=130° F.
Web speed: 2 feet per minute
Air Pressure: 3 inches of water.

D. Enzyme survival assay:

The conversion of 3,3',5, 5'-tetramethylbenzidine (TMB) to a colored product was expressed as the percent enzyme activity remaining of the liquid used to impregnate the paper matrix (Miles Technical Bulletin, 1983 and Bos, E. S., et al, 1981, J. Immunoassay 1:187.)

E. Performance survival assay:

The production of a given change in color, as percent reflectance (% R) between 0–40 micrograms/milliliter of theophylline on three layer strips, was expressed as the percent of the performance remaining of the liquid used to impregnate the paper matrix. Performance requires a functional antibody portion of the enzyme-antibody conjugate as well as the non-conjugated antibody added to the formulation.

Example I

A series of test runs was made using the base formulation, adding various salts to compare the effect on the recovery of HRP activity following the drying process (termed Loss on Processing, LOP) measured in terms of the percentage of a liquid control (% LC).

| Formulation | Salt | Concentration (mM) | % LC Enzyme (LOP) |
| --- | --- | --- | --- |
| 1 | None | — | 63.8 |
| 2 | EDTA | 10 | 77.4 |
| 3 | KCl | 100 | 69.8 |
| 4 | NaCl | 100 | 70.5 |
| 5 | $MnCl_2$ | 100 | 84.8 |
| 6 | $MnCl_2$ | 200 | 96.9 |

From the data, it is apparent that $MnCl_2$ performs significantly better than monovalent salts and sequestering agents, and it performs much better than no salt stabilizers at all.

Example II

A series of tests was conducted using the base formula and adding various metal salts. The following table shows the effect of these salts on enzyme and antibody survival after drying during storage for one week at 60° C. (termed Loss on Stress, LOS) measured in terms of % LC.

| Formulation | Salt | Concentration (mM) | Enzyme (LOP) | % LC Heat Stress Performance (LOS) |
| --- | --- | --- | --- | --- |
| 7 | None | — | 23.2 | 28.0 |
| 8 | NaCl | 100 | 36.6 | 56.8 |
| 9 | $MnCl_2$ | 100 | 59.8 | 60.3 |
| 10 | $MnCl_2$ | 200 | 92.8 | 95.3 |

Again, $MnCl_2$ performs significantly better than monovalent salts and much better than no salt stabilizer at all.

What is claimed is:

1. A stabilized, dry test strip for immunoassay produced by the steps comprising:
   (a) contacting a substrate with an aqueous solution comprising:
      (i) an enzyme-antibody conjugate, and
      (ii) a manganese ion in an amount sufficient for stabilizing the catalytic and binding activity of said conjugate whereby the conjugate and manganese ion are in an intimate association; and
   (b) drying the substrate at a temperature between 40°–100° C. whereby a manganese ion stabilized conjugate having stabilized catalytic activity and stabilized binding activity is disposed upon the substrate.

2. The stabilized, dry test strip of claim 1 in which the source of the manganese ion is a salt.

3. The stabilized, dry test strip of claim 2 in which the manganese salt is chloride.

4. The stabilized, dry test strip of claim 1 in which the substrate is paper, glass, fiberglass, agarose, nitrocellulose, polymeric material or mixtures thereof.

5. The stabilized, dry test strip of claim 4 in which the substrate is paper, nylon, dacron, fiberglass, agarose, nitrocellulose, polyacrylamide or mixtures thereof.

6. The stabilized, dry test strip of claim 1 in which the source of the manganese ion is present in a concentration up to about 1M.

7. The stabilized, dry test strip of claim 6 in which the source of the manganese ion is present in a concentration of from about 50 mM to about 500 mM.

8. The stabilized, dry test strip of claim 1 in which the drying temperature is from about 55° C. to about 80° C.

9. The stabilized, dry test strip of claim 1 in which the enzyme-antibody conjugate comprises a horseradish peroxidase-antibody conjugate.

10. The stabilized, dry test strip of claim 9 in which the horseradish peroxidase-antibody conjugate is a conjugate of horseradish peroxidase and the antibody specific to theophylline.

11. A device for determining the presence of analyte antigens comprising:
   (A) a matrix;
   (B) a first zone in the matrix comprising
      (i) bound and immobilized antigens, and
      (ii) manganese ion stabilized enzyme-antibody conjugates which are capable of reacting with the immobilized antigens or analyte antigens, the conjugates being positioned in the first zone such that they will be removed from the first zone when reacted with analyte antigens passing through the first zone but not removed from the first zone in the absence of such analyte antigens;
   (C) a second zone removed from the first zone containing a material capable of reacting with the enzyme-antibody conjugate to produce a color forming reaction which indicates the presence of the enzyme-antibody conjugate in the second zone which in turn indicates the presence of analyte antigens; the manganese ion stabilized enzyme-antibody conjugate being stabilized by the steps comprising:
      (a) forming an aqueous solution comprising:
         (i) an enzyme-antibody conjugate, and
         (ii) a source of manganese ion in an amount sufficient for stabilizing the catalytic and binding activity of said conjugate; and
      (b) drying the solution at a temperature between 40½°–100½° C. to form a manganese ion stabilized conjugate having stabilized catalytic activity and stabilized binding activity.

12. The device of claim 11 in which the source of the manganese ion is a salt.

13. The device of claim 11 in which the manganese salt is a chloride.

14. The device of claim 11 in which the source of the manganese ion is present in a concentration up to about 1M.

15. The device of claim 11 in which the source of the manganese ion is present in a concentration of from about 50 mM to about 500 mM.

16. The device of claim 11 in which the drying temperature is from about 55½° C. to about 80½° C.

17. The device of claim 11 in which the enzyme-antibody conjugate comprises a horseradish peroxidase-antibody conjugate.

18. The device of claim 17 in which the horseradish peroxidase-antibody conjugate is a conjugate of horseradish peroxidase and the antibody specific to theophylline.

19. A continuous method for the manufacture of a stabilized, dry test strip for immunoassay comprising:
   (a) contacting a continuous web substrate with an aqueous solution comprising:
      (i) an enzyme antibody conjugate, and
      (ii) a source of manganese ion in an amount sufficient for stabilizing the catalytic and binding activity of said conjugate whereby the conjugate and manganese ion are in intimate association; and
   (b) drying the continuous web substrate at a temperature between 40½°–100½° C. whereby a manganese ion stabilized conjugate having stabilized catalytic activity and stabilized binding activity is disposed upon the substrate.

20. The continuous method of claim 19 in which the source of the manganese ion is a salt.

21. The method of claim 20 in which the manganese salt is a chloride.

22. The method of claim 19 in which the source of the manganese ion is present at a concentration up to about 1M.

23. The method of claim 19 in which the source of the manganese ion is present at a concentration of from about 50 mM to about 500 mM.

24. The method of claim 19 in which the drying temperature is from about 55½° C. to about 80½° C.

25. The method of claim 19 in which a drying means comprising a heat tunnel with at least one heating zone is used in step (b).

26. The method of claim 25 in which the heat tunnel has three heating zones.

27. The method of claim 19 in which the dried continuous web is cut into strips for use in a multi-layer immunoassay test device.

28. The method of claim 19 in which the continuous web substrate is paper, fiberglass, agarose, nitrocellulose, polymeric material or mixtures thereof.

29. The method of claim 19 in which the continuous web substrate is paper, nylon, dacron, fiberglass, agarose, nitrocellulose, polyacrylamide or mixtures thereof.

30. The method of claim 19 in which the continuous web substrate is woven, non-woven or mixtures thereof.

31. The method of claim 30 in which the continuous web substrate is non-woven.

32. The method of claim 19 in which the enzyme-antibody conjugate comprises a horseradish peroxidase-antibody conjugate.

33. The method of claim 32 in which the horseradish peroxidase-antibody conjugate is a conjugate of horseradish peroxidase and the antibody specific to theophylline.

* * * * *